US006674862B1

(12) United States Patent
Magilen

(10) Patent No.: US 6,674,862 B1
(45) Date of Patent: Jan. 6, 2004

(54) METHOD AND APPARATUS FOR TESTING HEARING AND FITTING HEARING AIDS

(76) Inventor: Gilbert Magilen, 426 Virginia St., Vallejo, CA (US) 94590

( * ) Notice: Subject to any disclaimer, the term of this patent is extended or adjusted under 35 U.S.C. 154(b) by 575 days.

(21) Appl. No.: 09/724,361

(22) Filed: Nov. 28, 2000

Related U.S. Application Data

(60) Provisional application No. 60/169,590, filed on Dec. 8, 1999, and provisional application No. 60/168,947, filed on Dec. 3, 1999.

(51) Int. Cl.[7] ............................ H04R 29/00; A61B 5/00
(52) U.S. Cl. ........................................ 381/60; 600/559
(58) Field of Search ..................... 381/60, 58, 312, 381/316, 321; 600/559; 73/685; 128/864; 181/130, 135

(56) References Cited

U.S. PATENT DOCUMENTS

| 4,476,724 A | * | 10/1984 | Gotze ........................... 73/585 |
| 4,615,007 A | * | 9/1986 | King et al. .................. 600/559 |
| 5,386,475 A | * | 1/1995 | Birck et al. .................. 381/320 |
| 5,428,998 A | * | 7/1995 | Downs ........................ 73/585 |
| 5,811,681 A | * | 9/1998 | Braun et al. .................. 73/585 |
| 5,919,143 A | * | 7/1999 | Jenkins et al. .............. 600/549 |
| 6,056,698 A | * | 5/2000 | Iseberg et al. .............. 600/558 |
| 6,118,877 A | * | 9/2000 | Lindemann et al. .......... 381/60 |
| 6,496,585 B1 | * | 12/2002 | Margolis ...................... 381/60 |

* cited by examiner

Primary Examiner—Xu Mei

(57) ABSTRACT

A system and method for testing hearing or for testing and fitting hearing aids is provided, which includes at least one, and preferably a plurality of, compound multi-channel dynamic filters. The system is equipped with earphones, enabling the test operator to hear sounds transmitted to the subject simultaneously with the transmission. A signal is transmitted to the test operator that representing a condition in the patient's ear canal or canals. The test operator modifies the signal using the filter or filters to produce a transmitted signal conforming to and indicating the hearing loss of the subject. This information may then be used to adjust or fit a hearing prosthesis as appropriate, and can also be used to recognize a situation in which the subject's hearing is normal but the subject has lost capability to process sounds.

10 Claims, 3 Drawing Sheets

THE INVENTION

METHOD AND APPARATUS FOR TESTING HEARING AND FITTING HEARING AIDS

This is a continuation of provisional application Ser. No. 60/168,947 filed on Dec. 3, 1999 and Ser. No. 60/169,590 filed on Dec. 8, 1999.

BACKGROUND AND PRIOR ART

This invention relates to an improvement in methods for fitting hearing aids and to apparatus or equipment therefor.

In addition, this invention relates to methods and apparatus for testing and determining hearing abilities of a subject or patient, in general.

Advances in hearing aid technology and the technology of testing and fitting these devices have produced more sophisticated and accurate hearing aids as well as more sophisticated software for adjusting these devices. Nevertheless, there continues to be a substantial number of complaints by hearing aid wearers that, despite these improvements, the hearing aids do not function well. A frequently heard complaint of individuals with sensorineural hearing loss is "I hear, but I don't understand, especially in noise." This is still a principal complaint, even after having been fit with a hearing aid or after the hearing aid has been further adjusted. Indeed, recent observations have been that, despite the availability of better digital devices and the existence of professionals dispensing hearing aids, the overall hearing aid satisfaction rate has remained around 50% for in the past decade or so.

Currently, hearing aid fittings are validated by what are categorized in the industry as subjective and objective determinations. The most popular method for adjusting programmable hearing aids may be termed "simulated-objective" methods.

Common use of the term "subjective" as used in hearing aid industry refers to "experiential information to which the subject has 'privileged access'" (i.e., a third party cannot experience the thoughts of another individual directly, but can merely have access to that information via reports from the subject.) Subjective information is in that respect similar to thoughts, scents, visual and hearing experiences etc., of the subject. Because of the unverifiable nature of such reports, subjective information is generally considered to be of less validity than objective information.

Subjective measures include asking subjects to report the quality of their experience (e.g.: How does that sound?) and having the subject fill out a questionnaire aimed at determining the satisfactory nature of the instrument fitting.

The term "objective" is used to refer to information that can "be measured" by a third party, where "be measured" implies capable of being correlated to a proposed relevant scale. This class includes electro-acoustic measurements, psychometric tests and group clinical experimental results.

Objective measures include electro-acoustic measures by an instrument (e.g., analysis of the physical characteristics of the sound such as its intensity, frequency, etc, presented by the hearing aid in a test box; or as measured in situ with a probe microphone), speech discrimination tests (for instance, repetition of word lists), and sound field audiometry (determination of the improvement in hearing threshold with the hearing aid in the ear).

"Simulated-objective" methods include using computer simulations of what is expected to be the objective electro-acoustic response of the hearing aid, if the hearing aid were fit to an individual with an average size ear, and average acoustic resonance characteristics of that ear. Such methods are carried out with a physical coupling of the prosthesis in only one of many possible alternative couplings regarding canal depth, venting, coupler shape, etc. However, since these values are averages, the simulation normally does not match the response actually present in the ear canal of a particular individual, and in fact can differ by 10 dB, 20 dB or more in certain important frequency regions.

Most of the equipment used today by practitioners presents the objective or simulated-objective information in the form of data, for instance, as instrument readings, displays, computer simulations and the like.

This information is used by the hearing aid dispensing (and/or fitting) practitioner or a test operator to adjust the tuning characteristics of the instrument for each wearer. The more accurate the methods, the more appropriate the adjustments. However, the more objective the fitting methodology, the more technically challenging it is to the practitioner, and the less that methodology tends to be used by practitioners.

Currently, most hearing aid dispensing practitioners fit hearing aids and validate those fittings by the subjective method alone. Those who fit or dispense programmable hearing aids use a simulated-objective methodology. A small percentage use objective electro-acoustic verification methods, and a rare group use in situ measurements. Of those that use in situ measurements a small percentage use digital modulated sound signals that are capable of assessing the performance of the premium digital hearing instruments.

Some instruments are capable of monitoring the acoustic signal in situ in the ear. Some equipment is provided with earphones that may be plugged into the probe microphone system, to allow the dispensing test operator access to certain acoustic signals in the ear canal of the patient.

U.S. Pat. No. 6,056,698 of Iseberg, et al. discloses in concept apparatus for audibly monitoring the condition in the ear of a patient undergoing an auditory evaluation and a method of using that apparatus. This apparatus includes a signal generator for forming an electrical signal based on a condition within an ear (for instance, a probe microphone) and an output for making the signal accessible to an audio transducer (for instance a speaker or earphones connected to a jack on the apparatus). The test operator, in conducting the testing of the subject's hearing, is thus able to monitor the sounds in the subject's ear. Specifically, the apparatus allows the test operator to listen during the test for extraneous noises, for instance those produced by activities of the subject such as grinding of teeth. Alternatively, the apparatus may be used by the test operator in advance of testing the subject's hearing to identify environmental noise, or to listen to the test signal during testing.

Related to the invention is the concept of a hearing loss simulator. Hearing loss simulation has been used both in hearing research experimentation and to approximate for demonstration purposes what it would be like to hear with a hearing loss. In the experimental and demonstration usages, masking noise or a single channel gate (expander) filter, or a graphic equalizer have been used on pre-recorded test materials and presented to normal hearing subjects to compare to hearing impaired subjects.

SUMMARY OF THE INVENTION

This invention comprises both apparatus and method for testing hearing and for fitting or adjusting a hearing aid.

In general, the apparatus comprises:

a system for audibly monitoring and testing hearing of a subject by a test operator comprising:

a source of at least one test signal;

at least one probe for insertion into the ear canal of a subject;

at least one first speaker for emitting the test signal into one or both ears of the subject;

a signal generator or probe microphone system, for receiving from the one or both ears of the subject, via the probe, an audible signal representative of a condition within the one or both ears, and for generating therefrom an electrical signal;

an audio transducer for converting the electrical signal into an audible signal;

and at least one filter for filtering out low-level sound tones from the audible signal.

Another aspect of the invention relates to a method of testing the hearing of a subject. More specifically, this comprises:

A method for testing the hearing of a subject by a test operator, comprising:

establishing a threshold hearing level for the subject;

emitting at least one test signal simultaneously into one or both ears of the subject and one or both ears of the operator;

transmitting to the operator a signal from the ear canal or canals of the subject;

filtering low level sounds from the signal transmitted to the operator so as to substantially conform the transmitted signal to the threshold hearing level of the subject, producing a modified transmitted signal;

adjusting the transmitted signal to correspond to the supra-threshold loudness level experience of the subject; and comparing the modified transmitted signal with the full hearing range of a subject having normal hearing.

The method above can be further used to fit and/or adjust hearing aids by inserting a hearing aid into the ear of the subject after the comparison of the modified transmitted signal with the full hearing range of a normal subject, and by adjusting the hearing aid to compensate for hearing loss.

DETAILED DESCRIPTION OF THE INVENTION

Figure 1:
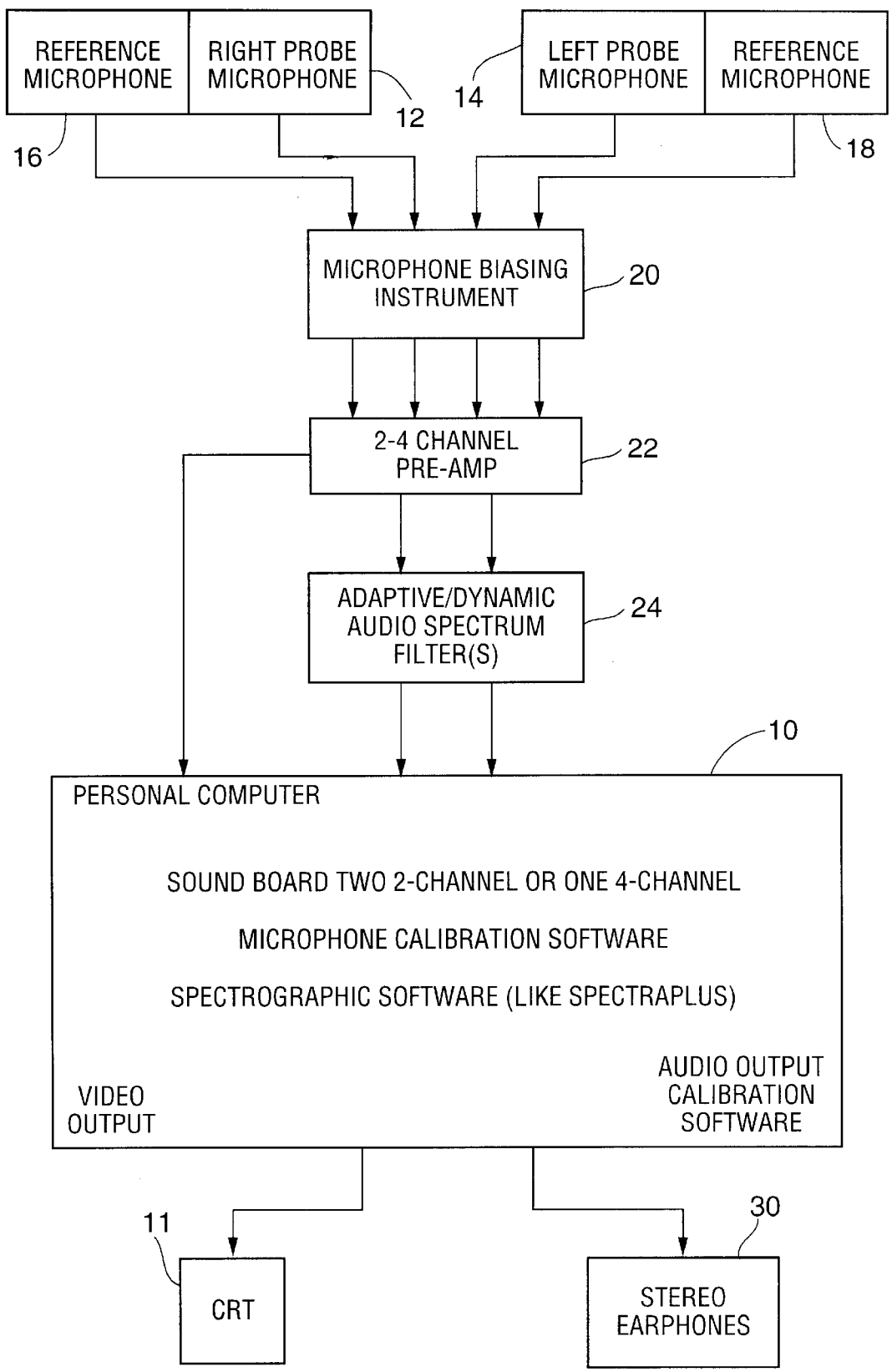
FIG. 1 represents a schematic of the system of this invention.

Instruments and techniques currently in use today tend to rely on demonstration of the hearing level of a subject to him or her and to the tester by means of displays, for example, computer-generated simulations or outputs of various measuring instruments.

Subjects may be asked for their subjective evaluation of their hearing aid's performance. In any given context the subject is more often than not unsure as to the appropriateness of the sounds they are hearing due to memory issues. Different contexts create additional confusions. Linguistic limitations of the subjects make it difficult for them to describe or communicate their auditory experience.

It has been my observation that individuals with sensorineural hearing loss have essentially the same supra-threshold sensitivities to sound as their normal hearing counterparts. Additionally, individuals who experience hearing loss can often hear middle-level and loud-level sounds the same as or even more than their counterparts with normal hearing levels. Indeed, for individuals having a hearing loss, relatively loud sounds may seem even louder than they do to others. What tends to be lost is the ability to hear very soft, or low-level, sounds, most often in a frequency-specific manner.

To properly fit a hearing aid or prosthesis, a test operator must be assured that acoustic cues are being delivered to the subject, and must be able to determine if the cues that are delivered are sufficient for an individual with normal auditory processing and cognitive capacities to achieve "understanding". This is because in a number of cases, a person's inability to properly understand, even with a hearing aid, may be due to lack of auditory processing or cognitive capacity, i.e., lack of capacity to properly process received sounds, as opposed to lack of physiological ability to receive and hear sounds. If the acoustic cues are provided in such a manner that a person with normal auditory processing and cognitive abilities is able to understand speech, yet the subject is still unable, this indicates such reduced auditory processing or cognitive capacity for the subject. If such diminished capacity is observed, then the test operator needs to further adjust the acoustic parameters of the hearing prostheses to optimize the presentation of the acoustic environment through the hearing prostheses to maximally benefit the subject's abilities.

The invention herein involves enabling the test operator testing for hearing level and/or fitting a hearing aid to experience sounds as heard by the subject or patient. As used herein, the term "test operator" refers to a person conducting a hearing test, whether for the purpose of fitting or adjusting a hearing aid, or for the purpose of general testing of a subject's hearing. The test operator may be a licensed hearing aid dispenser/audiologist, a medical doctor or a technician. By "subject" is meant the person whose hearing is being tested and/or who is being fitted with a hearing aid (or having an existing hearing aid adjusted). Speaking very generally, this is accomplished by providing an instrument having a means of generating a test signal simultaneously to a subject and to the test operator. This is preferably accomplished in the invention by providing earphones (or, alternatively, a speaker) to the test operator. Such earphones are provided as options with several instruments that are currently available. However, the invention herein involves a modification of instruments of this type, involving the incorporation of at least one, and preferably a plurality of, filters, preferably multi-channel adaptive, dynamic filters, that are capable of "real-time" modification of acoustic signals. As will be explained below, the use of such filters provides the test operator with access to an acoustic signal similar to what is delivered to the subject's brain as modified by the subject's damaged cochlea, which is not fully functioning.

In general, the system or apparatus of this invention comprises many of the components often found in apparatus sold for this purpose today. The system includes a source of at least one test signal, which is to be transmitted to the subject or patient as well as to the test operator. Currently available equipment includes mechanisms for generating many different types of test signals, including sounds, music, voices, with and without noise, and even includes means for providing simulated "real-life" situations, such as multiple conversations occurring at the same time in a single location. The test operator will choose the nature and intensity of signals to be transmitted to the subject for testing the subject's hearing in general and with a fitted prosthesis.

The equipment includes at least one probe for insertion into an ear canal of the subject, and at least one reference microphone. There is at least one speaker for emitting the test signal into the subject's ear. Thus, the test signal is transmitted to the subject.

The microphones are connected to a multi-channel preamplifier, and through that to a filter, (called a Hearing Loss Simulator) to a system including a computer having spectrographic software, audio input/output capabilities and stereo earphones (or speakers). The spectrographic software is capable of spectrographic analysis of the sound signal in intensity, frequency, time, phase and can perform distortion analysis etc., and is used to analyze the sound signal present in the ear canal of the subject.

The apparatus of this invention also includes a signal generator that receives from the ear an audio signal representing a condition within the ear canal. The signal generator, which may be a transducer, converts the condition within the patient's ear canal into an electrical signal. In this invention the signal is preferably delivered to earphones worn by the test operator. However, the transducer may alternatively be a speaker or other device that converts electrical signals to sound. The earphones or speaker are connected to the main apparatus via a typical output jack, or may be connected via hard wiring to the signal generator.

In this invention, the system or apparatus further includes at least one filter for filtering out low-level sound tones from the audible signal that is received by the signal generator in the subject's ear. The filters used in this invention are preferably multi-channel adaptive dynamic filters. Such filters are not new in general and have been sold for various purposes in electrical equipment. However, their use in apparatus for testing hearing and fitting hearing aids is novel, particularly when used to filter low-level noise from a signal being transmitted to the operator. Filters usable for this purpose in this invention have one or more of the following characteristics: gate (or expander) filters which remove low-level sounds, multi-channel dynamic spectral equalizers which can be shaped to given audio spectral contours, compressors which limit and contour the amplitude dynamic range, and temporal modifiers that add delays, reverberation or other temporal distortions. Such filters are found in TC Electronic's Finalizer.

While the system may include as few as one such filter, preferably it contains any number of filters necessary for the intended purpose of the test operator. The use of a plurality of filters is carried out in order to adjust the transmitted audio-signal to correspond to the wide range of clinically observed hearing losses. Such losses vary in the spectral shape of the hearing threshold and in spectral supra-threshold loudness sensitivities.

The system and apparatus of this invention may additionally contain other components currently found in such systems. These include, for example, computer monitors or other display devices, instruments for reading and displaying information on a screen, electrical signals simulating or representing the hearing of the subject.

FIG. 1 is a schematic depiction of a system according to this invention.

Referring to FIG. 1, the system comprises a personal computer (which may be a desktop or laptop computer, as desirable), generally indicated at 10. This contains, as is usual, one or more drives, a sound card, spectrographic software and also includes a monitor or other display device 11. Preferably the display device is a CRT output display that has capabilities of presenting audio spectra, speech spectrograms, a time series and other three-dimensional sound representations. The system includes means for generating one or more types of signals (not shown) which are to be transmitted to the subject during the testing.

Linked to the central computer 10 are a pair of binaurally balanced probe microphones 12, 14 and reference microphones 16, 18. The probe microphones are attached to probe tubes that are placed in the subject's ear canals; the reference microphones are placed along side each ear and are used to calibrate the probe microphones and assess bilateral calibrations.

The Microphone Biasing Instrument 20 adjusts the frequency response of the microphones to assure a flat frequency response. The pre-amplifier 22 (in this specific case, a 2–4 channel preamplifier) adjusts the transmitted signal gain from the biasing instrument 20 to have it electronically interface with the audio spectrum filter or filters, indicated at 24.

The component labeled "Adaptive/dynamic Audio Spectrum Filter" 24 is the actual "hearing loss simulator". It variously contains multi-channel (3–9 channel) spectral filters, low-level amplitude filters such as gate (expander) filters, mid and high amplitude filters such as compressors and limiters, and temporal filters such a delays, reverberation filters etc., which are used to adjust the contour of the frequency spectrum and amplitude ranges that are being transmitted from the probe microphone(s) 12, 14 that are situated in the subject's ear(s). These filters are capable of "real-time" modification of acoustic signals and allow a test operator to produce, as will be described below, an output signal which is derived from the original signal transmitted to the subject, minus a correction for the audibility sensitivities and supra-threshold deviations produced by the sensorineural damage to the individual's cochlea.

Also connected through the system is a set of stereo earphones 30. The probe microphones 12, 14 receive sound representative of the condition in the subject's ear or ears, and convert such sound to an electrical signal. That signal is transmitted through the system to earphones 30, or alternatively to a speaker. This enables the test operator to use his or her hearing to fit, select or adjust hearing aids based upon the received experience of the sound as existing in the subject's ear canal(s).

The method aspects of this invention comprise the steps of establishing a threshold hearing level for the subject, emitting at least one signal simultaneously into the ear of the subject and the ear of the operator, transmitting to the operator a signal representing a condition of the subject's ear canal, filtering low-level sounds from the signal transmitter to the operator so as to substantially conform the transmitted signal to the threshold hearing level of the subject (thereby producing a modified transmitted signal), modifying the transmitted signal to conform to the supra-threshold sensitivities of the subject, and (by the use, for example, of a filter bypass) comparing the modified transmitted signal with the full hearing range of a normal subject. This enables the operator to understand and appreciate the nature of the sounds actually heard by the subject, which is a far more accurate method of determining the subject's hearing than current techniques that use graphic and other depictions including computer simulations and readouts from various instruments.

Figure 2A:
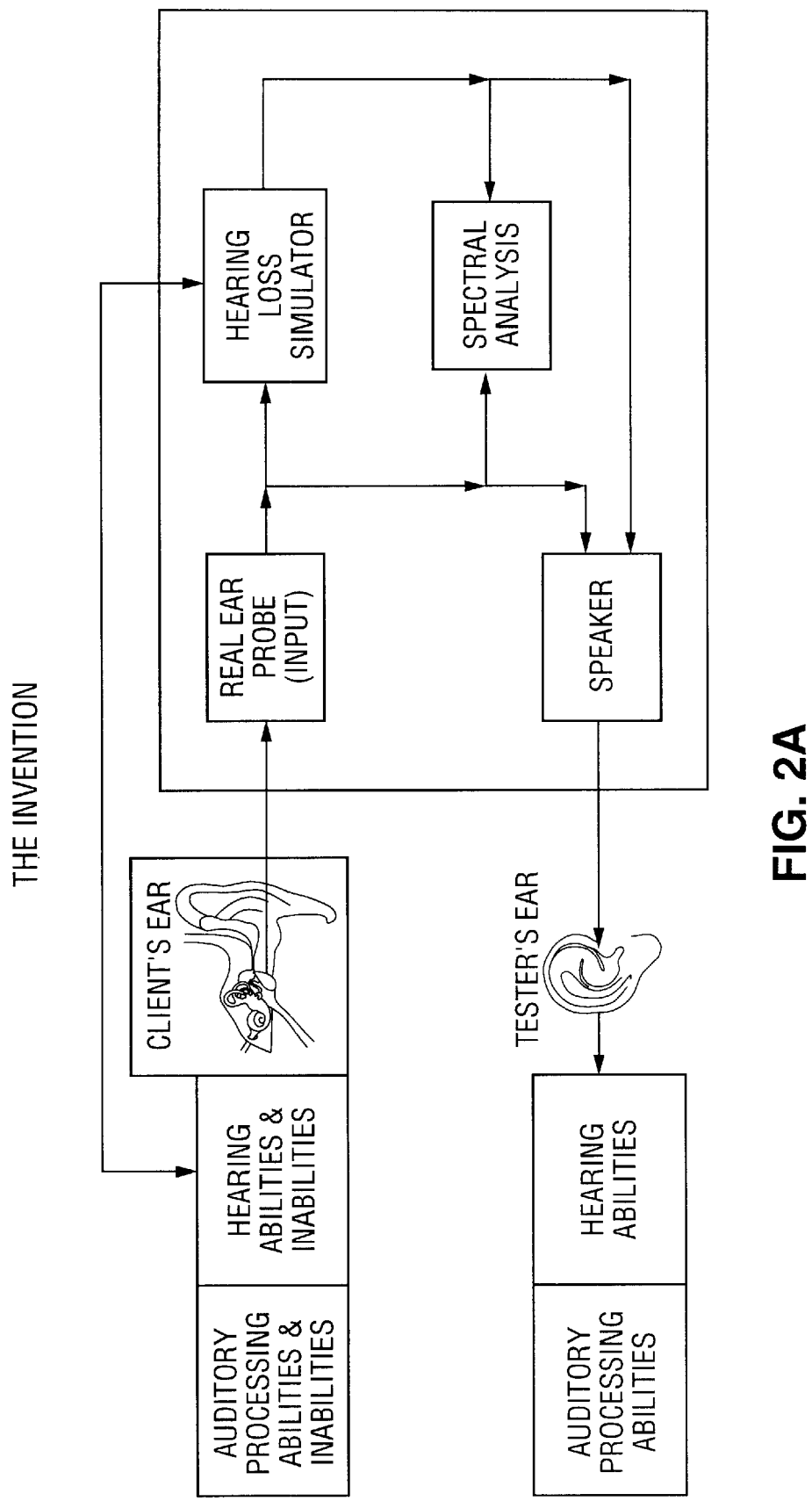
FIG. 2 represents comparative diagrams of prior art methods and instrumentation for fitting hearing aids, as compared with the system and method of the invention.
Figure 2B:
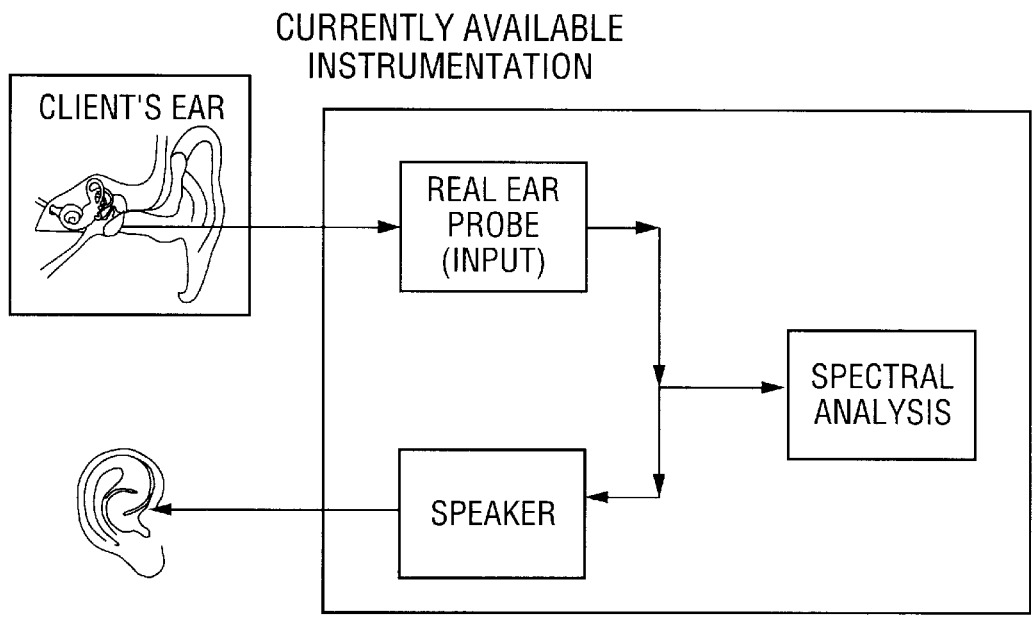
Figure 2C:
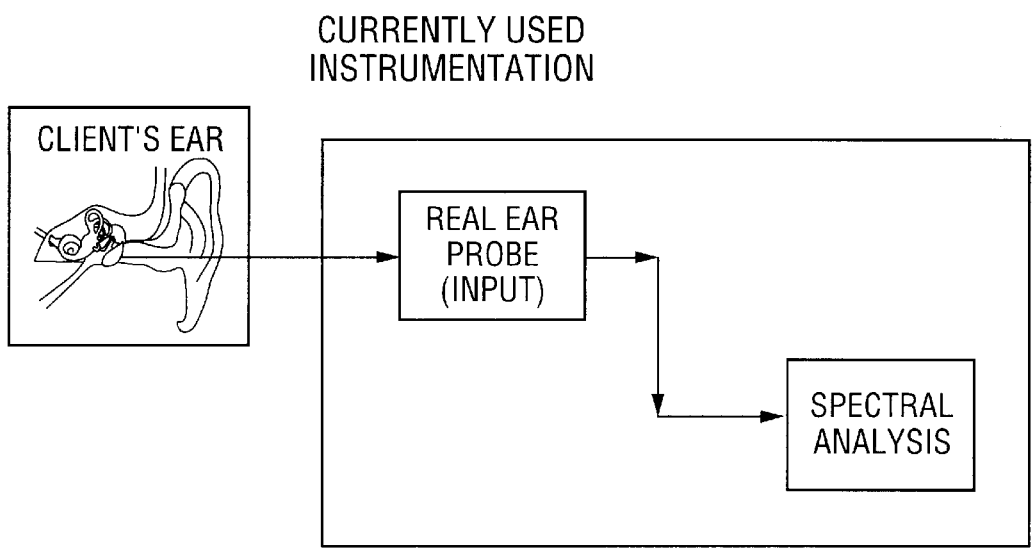

FIG. 2 graphically depicts the differences between the method described above and current instrumentation. FIG. 2c describes the usual instrumentation currently used for testing and fitting hearing aids, in which the sound from the subject's ear is transmitted via a probe through instruments performing spectral analysis, and is converted into an output, for example, instrument readouts or graphs shown on a computer screen.

FIG. 2b depicts a method disclosed in the Iseberg et al. U.S. Pat. No. 6,056,698 in which, in addition to converting sound in a subject's ear to a spectral analysis output, the test operator is able to monitor certain conditions in the ear (for example, the presence of environmental noise or noise generated by the subject) by use of a speaker or set of earphones.

FIG. 2a depicts the method of the present invention, which includes the generation of a signal to the test operator representing the actual sound condition within the subject's ear canals. As described herein, this enables the test operator to observe and account for not only physiological hearing ability and inability of the subject, but also for the subject's ability to process what is heard.

Current electro-acoustic measurement instrumentation cannot spectrographically demonstrate the presence of intelligible speech. It is in general not capable of distinguishing the degraded speech elements that contribute to speech discrimination, particularly in the presence of conflicting noise. However, the normal human auditory system is capable of such discrimination.

It has been my observation, as mentioned above, that individuals with mild and moderate sensorineural hearing loss, although lacking the audibility of normal hearing individuals, nevertheless retain a relatively normal range of hearing experience to mid and loud level sounds. The system, apparatus and method of this invention apparatus provides the test operator access to the acoustic signal delivered to the subject, modified in such manner as to correspond to the subject's hearing impairment and allows the use of the confirmed hearing of the acoustic and linguistic information in the subject's ear canal(s) as objective acoustic data. This modified signal can be assessed and evaluated by the test operator's own auditory processing system, as described above. The earphone presentation to the test operator can be calibrated to both the audibility loss of the subject as well as to any unusual loudness sensitivities. In this manner, the test operator is afforded the capability of modifying and assessing the quality of a hearing aid fitting as well as the capabilities of the subject, utilizing as a comparison the test operator's own speech discriminating ability.

The test operator also can use his or her own higher-level auditory processing and cognitive abilities to process subtle co-modulated speech patterns, timbre features, spectral characteristics, etc., in the signal transmitted to the subject (for instance a statement in the test operator's own voice) to assess the availability of specific types of speech cues in the subject's ear canal(s). If the subject hears, but does not understand the presented speech and the test operator does, this indicates that although equal audibility has been provided, higher-level processing abnormalities are limiting intelligibility for the subject.

For instance, the test operator can assess faculties such as speech discrimination—under a variety of environmental conditions, with different speakers, or with different speaking rates; "hearing out" signals in noise; echo suppression; directional determinations; segregation of competing sound/ speech signals, and integration of associated sound/speech signals. The test operator may also be able to assess for sound quality judgements, for example judgements based on missing or distorted sound components or on timbre variations from the norm.

More specifically, the method of this invention is carried out in the following manner:

First, audiometric tests are performed in order to establish the hearing threshold and general supra-threshold sensitivity levels of the subject.

The probe microphones are then placed in the subject's ear or ears and a hearing prosthesis whose settings roughly approximate an average hearing loss correction is placed in the ear(s). The subject is asked to adjust the general volume control level to what he or she considers a natural conversational level. The test operator listens to the signal transmitted from the subject's ear canal via the earphones. Then appropriate threshold level sounds are simultaneously presented to the subject and the test operator listening to the signal from the subject's ear canal. If a test signal is just barely audible to the subject, then the test operator adjusts the parameters on the multi-channel dynamic filter (the hearing loss simulator) so that the test signals are just barely audible to the test operator. Similarly the parameters of the hearing loss simulator are adjusted to provide conformity with the supra-threshold loudness sensitivities of the subject and the test operator to a variety of test signals of varying strength and spectral complexity.

The method of using the filters comprises, for example, using the volume control to set the comfortable level for average sounds; using the threshold low-level sounds for setting the gate filter; and using the suprathreshold medium and loud sounds for setting the compressor and output limiter.

Then the hearing prosthesis is adjusted with the use of standardized speech-like signals (for example ICRA, DSP, etc.) and/or live voice signals and/or other types of sound signals. The test operator simultaneously monitors the test signals with the spectrographic output from the apparatus and with the earphones. Software is used to display corresponding fitting target curves on a spectrogram, in addition to output obtained from the ear canal.

The filters on the hearing prosthesis are then adjusted to provide gain for soft sound (to provide adequate audibility to various soft voices or speech modulated noise patterns) and provide squelch (low-level expansion) to compensate for soft, non-speech noises. Additionally, the filters are used to provide appropriate gain if necessary for loud ("alarm clock") sounds of varying intensities and durations in each manageable frequency channel.

Preferably the test signal battery also contains at least four signals representing speech, which are used to present speech modulated tonal/noise patterns of different spectral composition (i.e., representing different voice qualities). These different voice spectral filters may be used to create sentence lists for testing the subject. The hearing instruments are tuned to maximize speech intelligibility to the four voices. The audio-visual appearances of the speech modulated noise patterns and voice spectra are determined. Continuous multi-talker in speech babble noise, or other simulated noise environments appropriate to the subject's lifestyle, may be played at different noise levels. Signal/ noise ratios vs. intelligibility tests can be performed to determine threshold of intelligibility and the best prosthesis settings for optimal intelligibility for the different environmental noise contexts.

Special auditory signal processing tests can be used to assess higher level processing problems in the subject. These can range from standard auditory processing tests to more experimental speech degradation tests, in which running speech is presented with increasingly desynchronized speech until the subject is no longer able to repeat the sentences.

"Quality of Sound" complaints from the subject can be also be analyzed by auditory monitoring by the test operator and by comparing the waveform characteristics of the probe and reference microphones after presentation of the questionable sound.

Using this instrument and method the test operator can modify or replace the prosthesis to optimize its performance for the subject's needs. The test operator can determine whether the subject's inability to hear or understand is due to limitations of the hearing prosthesis or to limitations of the client's auditory processing or cognitive capacities. This methodology can substantially restore the subject's hearing and understanding and presumably the subject is satisfied. In multiple memory hearing instruments or to test certain adaptive features, the entire procedure is repeated to adjust the hearing instrument under appropriate conditions.

On the other hand, if replacement or adjustment of the prosthesis still does not compensate for the patient's inability to hear, then it is likely that the patient's inability to hear is not due to a physiological condition that can be corrected by amplifying the sound appropriately, or is due at least in part to a lack of auditory processing or cognitive abilities to process sounds. Since the test operator can establish whether he or she is able to properly process the same sounds, a comparison of the test operator's abilities with that of the subject will indicate that the auditory processing and cognitive capabilities of the subject have been adversely affected. In that case, the test operator will so advise the subject.

Subjects whose performance is not adequate with hearing prostheses alone may require the use of assistive listening devices (ALDs) such as special remote microphone transmitters, supplemental beam forming microphone attachments, special telephone adapters or other audio input devices. The performance of each of these may be evaluated for the subject via the use of this invention.

It should be noted that the use of the filters used in this invention differ substantially from the use or adjustment of sound level in current equipment. Adjustment of sound level in current equipment is performed similarly to adjustment of sound level in a stereophonic system. That is, the operator is able to separately adjust the volume of low-frequency (bass) or high-frequency (treble) sounds or any other sounds that the equipment is capable of adjusting. Similarly, equalizers may be used to balance general sound levels. The test operator could also balance the two different types of sounds as is normally done in using stereophonic equipment. However, in all of these methods, whether the volume is lowered or raised, all the qualities of the bass or treble sounds respectively are retained, from low-level to high-level sounds of that type. On the other hand, the use of the present system and method enables the test operator to block or filter out low-level sounds of a specified type (depending on the filters that are used) entirely or nearly entirely. This filtering out more accurately replicates a subject's actual hearing experience, since loss of hearing tends to lie primarily if not entirely in the loss of ability to hear low-level sounds most often restricted to a particular (e.g.: high frequency) region of the frequency spectrum. The capabilities of the system and apparatus, and method, of this invention to utilize this procedure so as to make it possible for the operator to experience the actual hearing loss or ability of the subject, provides a distinguishing feature over current or other prior art techniques and equipment.

Modifications and variations of this invention may be readily apparent to those skilled in the art from this description. Therefore, my invention is not limited to the specific features as disclosed herein but only to the invention as claimed in the claims that follow.

What is claimed is:

1. A system for audibly monitoring and testing hearing of a subject by a test operator comprising:

a source of at least one test signal;

at least one probe for insertion into the ear canal of a subject;

at least one first speaker for emitting the test signal into the ear of the subject;

a signal generator for receiving from the ear via a probe, an audible signal representative of a condition within the ear, and for generating therefrom an electrical signal;

an audio transducer for converting the electrical signal into an audible signal;

and at least one filter for filtering out low-level sound tones from the audible signal.

2. A system according to claim 1 in which the test signal comprises one or more live voice signals.

3. A system according to claim 2 in which the live voice signals comprise speech modulated noise patterns of different spectral composition representing different voice qualities.

4. A system according to claim 1 in which the signal generator comprises a probe microphone.

5. A system according to claim 1 in which the transducer comprises an earphone or earphones.

6. A system according to claim 1 further comprising spectral display means for displaying sound qualities.

7. A system according to claim 1 comprising a plurality of filters.

8. A method for testing the hearing of a subject by a test operator, comprising:

establishing a threshold hearing level for the subject;

emitting at least one test signal simultaneously into one or both ears of the subject and of the operator;

transmitting to the operator a signal from the ear canal or canals of the subject;

filtering low level sounds from the signal transmitted to the operator so as to substantially conform the transmitted signal to the threshold hearing level of the subject, producing a modified transmitted signal;

adjusting the transmitted signal to correspond to the supra-threshold loudness level experience of the subject; and comparing the modified transmitted signal with the full hearing range of a subject having normal hearing.

9. A method according to claim 8 in which the test signal comprises a live voice signal or signals.

10. A method according to claim 8, further comprising adjusting an existing hearing prosthesis for the subject or fitting the subject with a new prosthesis.

* * * * *